United States Patent [19]

Mickaels et al.

[11] Patent Number: 5,224,058
[45] Date of Patent: Jun. 29, 1993

[54] METHOD FOR DATA TRANSFORMATION

[75] Inventors: Ronald A. Mickaels; Richard K. Dost, both of Mountain View; Leon W. M. M. Terstappen, Palo Alto; Michael R. Loken, Los Altos, all of Calif.

[73] Assignee: Becton, Dickinson and Company, Franklin Lakes, N.J.

[21] Appl. No.: 517,096

[22] Filed: May 1, 1990

[51] Int. Cl.$^5$ .............................................. G06F 15/20
[52] U.S. Cl. ........................................ 364/554; 356/39; 364/413.07; 364/550; 422/82.08
[58] Field of Search ................ 356/39, 338, 339, 342, 356/442; 364/413.07, 550, 554; 422/82.08, 82.09; 436/805

[56] References Cited

U.S. PATENT DOCUMENTS

| 3,826,364 | 7/1974 | Banner et al. ........................ 356/73 X |
| 4,284,412 | 8/1981 | Hansen et al. ....................... 356/39 X |
| 4,596,035 | 6/1986 | Gershman et al. ................... 356/39 X |
| 4,661,913 | 4/1987 | Wu et al. ............................. 364/550 X |
| 4,662,742 | 5/1987 | Chupp ................................. 356/73 X |
| 4,727,020 | 2/1988 | Recktenwald ....................... 356/39 X |
| 4,845,653 | 7/1989 | Conrad et al. ...................... 364/521 |
| 4,876,190 | 10/1989 | Recktenwald ..................... 436/800 X |
| 4,987,086 | 1/1991 | Brosnan et al. .................... 356/39 X |
| 4,989,977 | 2/1991 | North, Jr. ........................... 356/338 |

OTHER PUBLICATIONS

Herzenberg et al., Sci. Amer., 234:108 (1976), pp. 108–117.

Primary Examiner—Edward R. Cosimano
Attorney, Agent, or Firm—Robert M. Hallenbeck

[57] ABSTRACT

A method for the non-linear, non-logrithmic transformation of one or more parameters of data gathered by means of flow cytometry is disclosed wherein the method seeks to maximize the resolution between populations of interest for each parameter while maintaining the dynamic range of the data recorded.

10 Claims, 6 Drawing Sheets

ORTHOGONAL LIGHT SCATTER

FORWARD LIGHT SCATTER

CD4 PE

CD16 FITC

ORTHOGONAL LIGHT SCATTER

METHOD FOR DATA TRANSFORMATION

The file of this patent contains at least one drawing executed in color. Copies of this patent with color drawings will be provided by the Patent and Trademark Office upon request and payment of the necessary fee.

FIELD OF THE INVENTION

This invention relates to the transformation of multiparameter data, and more particularly relates to the transformation of multiparameter data collected from cells by means of flow cytometry for the purpose of improving the visualization and analysis of data collected.

BACKGROUND OF THE INVENTION

There are a number of methods that presently exist to analyze multiparameter data. These methods all rely on some form of mathematical modeling which is used to present, rearrange or transform the data in such a way that observations may be made and conclusions drawn. Such methods include multivariate analysis, regression analysis, logrithmic transformation, etc. While such methods generally are not dependent upon the manner of data collection, in many instances those who collect data by a particular method routinely use the same form(s) of data analysis and presentation. This is especially true in the field of flow cytometry.

Flow cytometry and flow cytometers generally are described in U.S. Pat. Nos. 4,661,913, 4,284,412, and 3,826,364, and in an article by Herzenberg et al., Sci. Amer., 234:108 (1976). In principle, they operate to identify different populations of cells, typically leukocytes, in a heterogeneous cell sample, such as blood or bone marrow, by detecting multiple independent parameters on the individual cells that pass through one or more sensing regions substantially one at a time. Each sensing region essentially comprises an area illuminated by the light of a single wavelength and from which light is collected by an array of photomultiplier tubes. Each photomultiplier tube measures a separate parameter. Typically, these parameters include forward light scatter (or FLS, which is a measure of relative particle size), orthogonal light scatter (or OLS, which is a measure of relative granularity or special complexity) and fluorescence emission(s) (generally referred to as FL1, etc.).

Fluorescence may be measured from cells that incorporate a nucleic acid stain and/or may be measured from cells bearing surface or cytoplasmic markers which are labelled with monoclonal antibodies which have been conjugated directly or indirectly with fluorochromes. In the indirect method, for example, fluorescently labelled goat anti mouse antibodies are used as a second step reagent to detect the presence of the mouse derived primary monoclonal antibodies which react with the antigen of interest. Fluorochromes and stains may be referred to as fluorescent labels.

In order to identify specific cells in a heterogeneous population bearing one or more specific antigens, antibodies specific to those antigens are conjugated to fluorescent labels which have different emission spectra and, preferentially, are excitable at the same wavelength of excitation. Two labels having these properties are the fluorochromes fluorescein isothiocyanate (FITC) and phycoerythrin (PE). Other pairs of fluorochromes may be selected from the group consisting of FITC, phycoerythrin, Texas red (Molecular Probes), C-phycocyanine, allo- phycocyanine, and peridin-chlorophyll complex.

Cells reacted with the fluorescently labelled monoclonal antibodies then are examined using means to excite the fluorochromes present and to detect the fluorochrome emissions. Preferentially, such means comprise a flow cytometer wherein treated cells are passed substantially one at a time through a sensing region where light of excitation wavelength illuminates each cell and further wherein scattered light and fluorescence emitted by each cell is collected, recorded and stored in associated hardware and software. The fluorescent emission and light scatter data so recorded for each cell then may be analyzed by means of complex programs which can correlate the differential light scatter and fluorescence intensities for each of the cell types treated.

It is important that if more than one fluorescent label is used that each label have a different wavelength of emission in order that fluorescence emission from each will minimally overlap. Generally, FITC and PE meet this criteria and are used. It is preferable that the labels also be excitable at the same wavelength. This allows the cells to be in the sample to be passed through one sensing region and exposed to light of a single wavelength (e.g., from an argon laser at 488nm). In other embodiments, the flow cytometer may have more than one sensing region. In one such embodiment, a dual laser source may be used where the labels selected are not excitable at the same wavelength.

Separate detector channels within the flow cytometer are able to sense light emitted or scattered for each of the various cell parameter measurements. In a typical configuration, four or more parameters are measured (e.g., FLS, OLS, FL1 & FL2). Signals from these detectors for each cell passing through the sensing region are collected and may be stored for later data analysis by appropriately equipped recording means (e.g., a personal computer) and software (e.g., Consort 30 software or FACScan Research software, BDIS). By combining and comparing these parameters, the various leukocyte components may be identified and distinguished. U.S. Pat. No. 4,727,020 provides one example of how a flow cytometer may be used in this method to obtain leukocyte differentials from blood.

In that patent, the data collected for cells labelled by a certain fluorescent marker is presented in FIG. 2 as a histogram of log fluorescence. FIG. 3 of that patent further shows a dot plot of cells labelled by two fluorescent markers.

In U.S. Pat. No. 4,876,190, data was collected for cells labelled with a new fluorescent conjugate, PerCP. As seen in FIG. 1 of that patent, OLS is plotted versus FLS in order to discriminate between cells. The other figures in that patent are similar to those set forth in the prior mentioned patent.

In both examples, the purpose for displaying the data is to discriminate between cells of different lineages or maturational stages (e.g., between cells of myeloid versus lymphoid lineage and/or between mature and immature leukocytes). When data is presented, often one seeks to draw or define a gate around a particular population of interest, as shown in FIG. 1 of the later mentioned patent, and then to analyze separately the cells that fall within (or outside) that boundary (or gate).

Often times, however, the separation of the data is not sufficient to clearly establish this boundary such that there can be a clear distinction between cells of different types. In this case, when a boundary is defined, more (or fewer) cells will be included (or excluded) from the gate than is desired. What is needed is a method to transform the data collected in such a way that the cells of interest are more readily distinguishable from the cells of lesser or no interest without adversely effecting overall information content. The difficulty, however, is to increase the resolution within a given region of interest without sacrificing the dynamic range or losing other information contained in the data.

SUMMARY OF THE INVENTION

This invention comprises a method for the transformation of data which enables the user to maximize the presentation of data of interest and reduce (or minimize) the presentation of data of lesser interest This invention is particularly useful in the analysis of data collected by means of flow cytometry wherein data collected for light scatter and/or fluorescence intensity is transformed to enhance (or maximize) resolution for presentation of data for one or more types of cells of interest and to reduce the presentation of data for cells of lesser interest without sacrificing information contained within the sample.

The method of data transformation involves the arbitrary selection of a new scale for one axis of data presentation such that the presentation of data for one or more types of cells of interest is maximized and the presentation of data for cells of lesser interest is minimized. In other words, the selection of the new scale seeks to maximize the dynamic range of the data as well as resolution. The scale also must be selected so that it includes all data (i.e., none of the data is lost off the scale selected.) Once the scale is selected, a line or curve is modeled to fit through the points plotted. The formula for the line or curve that best fits the points plotted then is used to transform all the data collected for the cells in the sample. In this way, when the transformed data is plotted, more information can be garnered from the data.

DETAILED DESCRIPTION

Figure 1A:
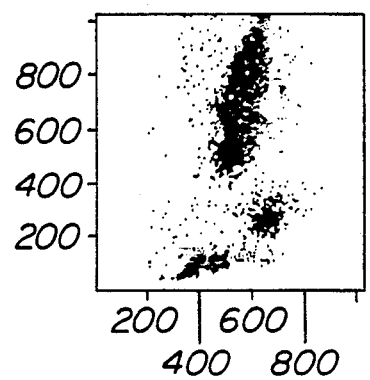
FIG. 1 comprises several plots of normal peripheral blood leukocytes labelled with anti CD4 PE and anti CD16 FITC monoclonal antibodies when analyzed by flow cytometry wherein FIG. 1A comprises a dot plot of OLS versus FLS, FIG. 1B comprises a dot plot of log PE versus log FITC fluorescence, FIG. 1C comprises a histogram of OLS and FIG. 1D comprises a histogram of OLS for the same cells in FIG. 1C when gain is increased.

Multidimensional flow cytometry identifies cell populations as clusters in a space created by the analysis of multiple parameters simultaneously. Optimal use of multidimensional space requires each of the individual parameters to provide additional information for cell population discrimination, as well as maximum utilization of a dynamic range available for each parameter. Because data can be visualized only in two dimensions, improving the visualization of multidimensional information present in light scatter and/or fluorescence signals are necessary to facilitate analysis.

Using light scatter as an example, it is known that light scattering properties of human leukocytes in flow cytometry may be used for the discrimination between lymphocytes, monocytes and granulocytes. The dynamic range of OLS does not permit simultaneous resolution of the different types of lymphocytes observed within the lymphocyte population and visualization of neutrophils on the same linear scale. To resolve and discriminate populations within lymphocytes and to more readily discriminate them from neutrophils, it is possible to transform the OLS signals by applying the method described below to provide a more equal distribution of leukocyte populations in a light scatter display. This transformation expands the resolution among lymphocytes while maintaining the dynamic range necessary to also observe neutrophils. As a result, clusters of cells are repositioned in multidimensional space resulting in an optimal separation of the cell populations present in the cell preparation.

Peripheral blood of healthy normal human donors was collected by venipuncture into evacuated blood collection tubes containing ethylenediamenetetracetic acid $K_3$ (EDTA) as an anticoagulant. For the lysis of erythrocytes in the sample, one volume of blood was mixed with fifteen volumes of a lysing solution comprising $10^{-4}$ M EDTA, $10^{-3}$ M $KHCO_3$, 0.17 M $NH_4Cl$ in $H_2O$ (pH 7.3) and gently mixed. Cells were lysed for 3-5 minutes and then centrifuged at 200 g for 5 minutes at room temperature. The pellet was resuspended in a final volume of RPMI 1640 at 14 times larger the original blood volume and centrifuged at 200 g for 5 minutes. This washing step was repeated twice and the cells were finally resuspended in phosphate buffered saline containing 1% bovine serum albumin and 20 mM Hepes (pH 7.3). The cell concentration was adjusted to $1 \times 10^7$/ml. Twenty μl of pre-titered monoclonal antibodies were added to 100 μl of cell suspension. After incubating for 20 minutes on ice, the cells were washed once with 3 ml of the PBS solution at 4° C. The staining procedure was repeated for the following staining steps. The fluorescently labelled monoclonal antibodies were added at the last staining step. The pellet of the immunofluorescent labelled cells was resuspended in 1 ml of 1% paraformaldehyde in PBS. 10 μl of the nucleic acid dye LDS 751 (Exciton) was added to the fixed cells.

The monoclonal antibodies anti CD4 PE (commercially available as anti Leu 3a, BDIS) and anti CD16 FITC (commercially available as anti Leu 11a, BDIS) were used. Cytophilic IgE was detected with a biotinylated polyclonal anti-human antibody (KPL) using streptavidin phycoerythrin (BDIS) as a second step reagent.

Flow cytometric analysis was performed on a FACScan brand flow cytometer (BDIS). Data acquisition was performed in listmode with FACScan Research software (BDIS). FLS, OLS and three fluorescence signals were determined for each passing event, distributed over 1024 channels and stored in listmode. By gating on LDS 751 fluorescence intensity, only intact nucleated cells were stored in the data files.

The listmode data was analyzed with the Paint-A-Gate software (BDIS) which is more fully described in U.S. Pat. No. 4,845,653. Briefly, this program utilizes three primary colors and four secondary colors to identify cell clusters in two parameter projections of the data. Once a cell cluster is identified with respect to the parameters used for analysis, a specific color can be assigned to a population. After removing the colors used for the identification of one cluster, other clusters also may be identified.

Figure 1C:
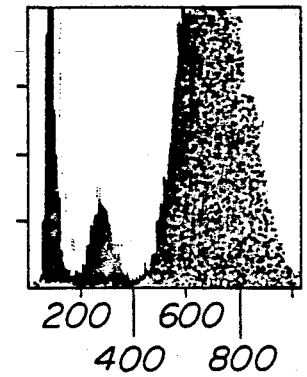
Figure 1B:
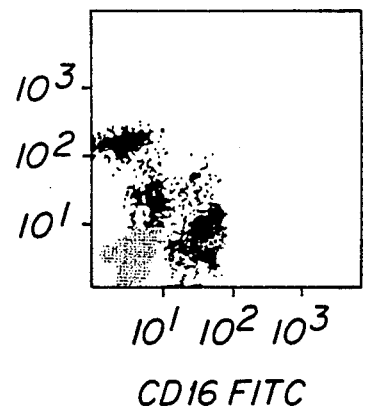

Referring to FIGS. 1A and 1B cells of different lineages were identified as follows by immunofluorescence and light scatter signals: lymphocytes were painted dark blue; monocytes were painted red; neutrophils and NK cells were painted green; and lymphocytes not staining with either anti-CD4 PE or anti-CD16 FITC were painted gray.

Figure 1D:
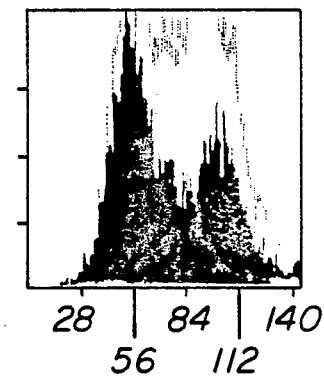

In FIG. 1C, it can be seen that the neutrophil population dominates in a linear display histogram of OLS. This linear display obscures the resolution between lymphocytes and NK cells when the gain is increased as in FIG. 1D. In this display, only the lymphocytes are displayed, while the monocytes and neutrophils appear in the last channel off scale. NK cells (identified as CD16+ cells and colored blue) have distinctly larger OLS signals as compared to helper lymphocytes (identified as CD4+ and colored green). The light blue color indicates that populations identified as dark blue and green based on immunofluorescence overlap in their OLS. The gray line on top of the painted areas represents the histogram of OLS signals of lymphocytes not identified by either monoclonal antibody.

Figure 2A:
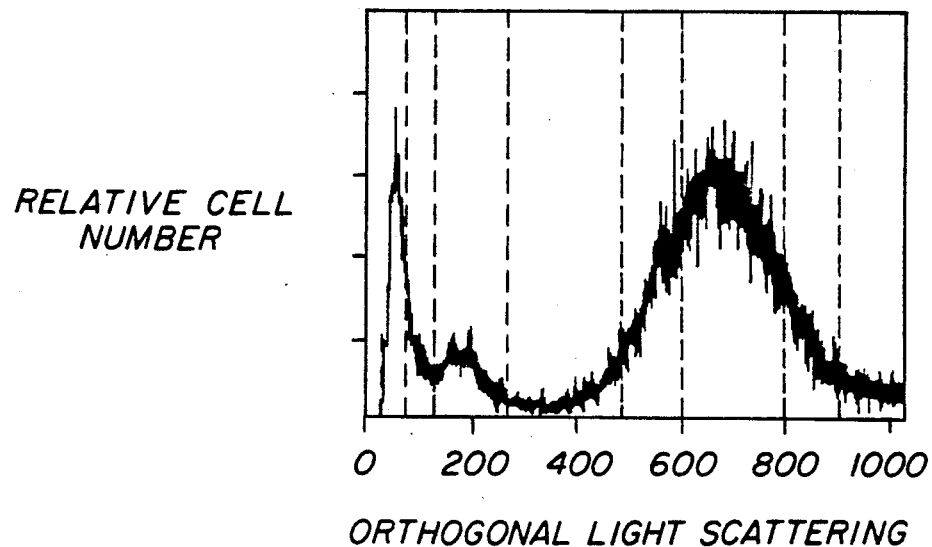
FIG. 2A comprises a histogram of OLS for the populations of cells from FIG. 1 and FIG. 2B comprises a plot of transformed channel number versus OLS channel number for the populations identified in FIG. 2A.

As the present dynamic range of linear amplified OLS signals does not permit a simultaneous visual separation of non-granular lymphocytes, granular lymphocytes, monocytes and granulocytes, the data was transformed to maximize the separation or resolution in one region of OLS while deemphasizing or minimizing the resolution of other regions. In order to transform the data, a histogram of OLS for the populations of interest was prepared. Referring to FIG. 2A, from left to right, a linear display positions the non granular lymphocytes, granular lymphocytes, monocytes, a region between monocytes and granulocytes and a granulocytic region as shown. As can be seen, the visual separation between the non granular lymphocytes, granular lymphocytes and monocytes is minimal making resolution between these populations based on OLS difficult. On the other hand, the separation between the granulocytes and the remaining populations is clear.

To maximize the separation between these compacted populations and minimize or deemphasize the importance of the granulocyte population, dotted lines were drawn in FIG. 2A indicating the approximate boundaries between the populations. Precisely where these lines are drawn is not critical to the practice of this invention; however, the lines should be drawn to approximate the boundaries. It is appreciated by those skilled in the art where those boundaries lay for each parameter. In the event a new parameter or new sample is being examined, the cells in the sample can be sorted and examined morphologically in order to obtain an approximation of the boundaries between cell types.

Figure 2B:
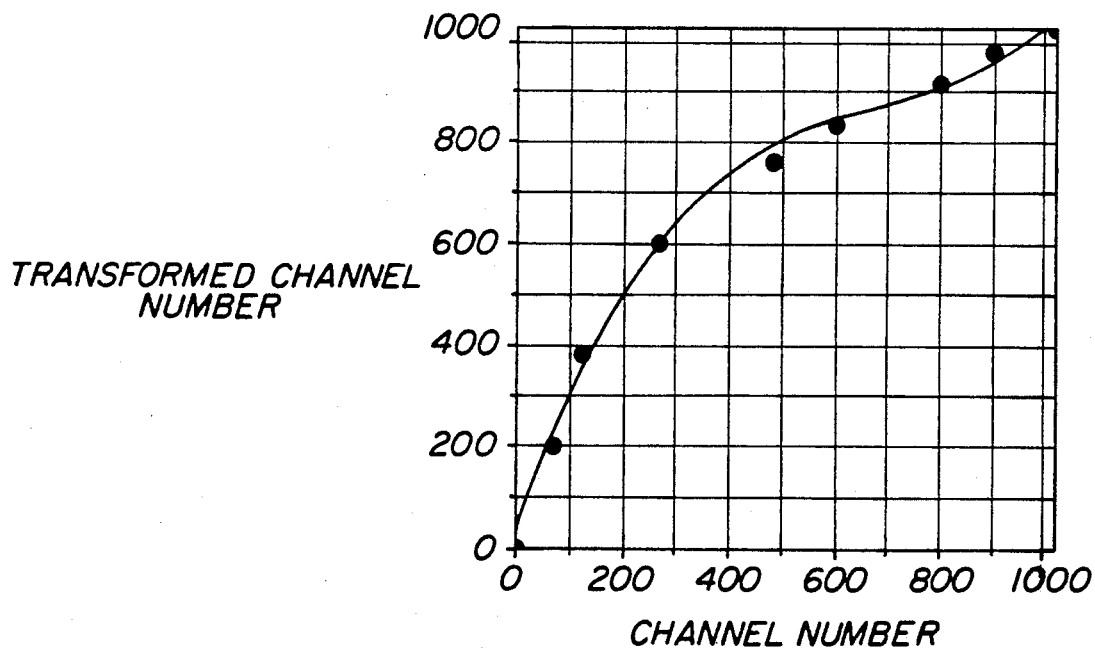

The next step is to take the positions where the dotted lines cross the X axis in FIG. 2A and to plot them along the X axis in FIG. 2B. An arbitrary transformed scale then is constructed for the Y axis and each point corresponding to a dotted line is plotted on the Y axis to maximize separation. It will be appreciated that other points, corresponding to points within a population, also can plotted. Thus, for example, wherein the first dotted line in FIG. 2A has a mean channel number of approximately 80 when plotted along the transformed Y axis the channel number is arbitrarily selected as 200. Taking the next dotted line, the line is arbitrarily plotted along the transformed axis at approximately 380. The same is done for each other point along the X axis.

As can be seen from FIG. 2B, the distance between points along the Y axis now varies from 0 to 600 whereas in the untransformed X axis the separation is between 0 and approximately 370. For the points corresponding to the monocyte-granulocyte regions, there is less necessity to maximize the separation of these points. Accordingly, the separation of these points along the X axis is compressed along the Y axis. Overall, one can see in FIG. 2B a curve or line having a slope significantly greater than 1 initially but then falling below 1.

The function that fits this particular line was calculated by a best fit through the points using a program STATSVIEW (Abacus Concepts Inc.). The best fit for this particular curve was calculated as $y = 14.96 + 3.09X - 0.004X^2 + 0.0000019X^3$. Using the best fit formula, for example, a monocyte occurring at channel 200 will be displayed at channel 500 after transformation.

Figure 3A:
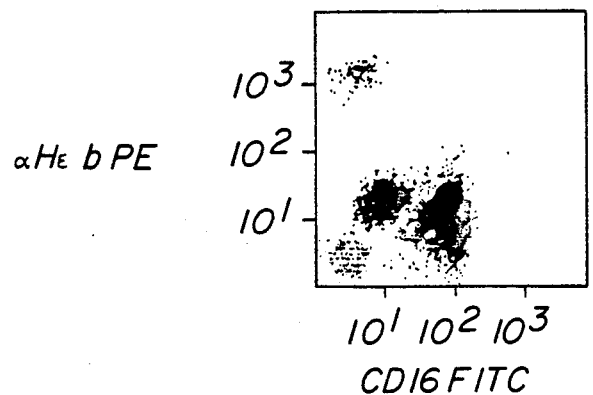
FIG. 3 comprises a series of dot plots for normal peripheral blood leukocytes labelled with anti-Human IgE biotin/PE and anti CD16 FITC monoclonal antibodies when combined with the fluorescent nucleic acid stain LDS-751 and analyzed by flow cytometry wherein FIG. 3A comprises log fluorescence intensity of PE versus FITC, FIG. 3B comprises log fluorescence intensity of LDS-751 versus PE, FIG. 3C comprises OLS versus FLS, FIG. 3D comprises transformed OLS versus non-transformed FLS FIG. 3E comprises log PE fluorescence versus OLS, FIG. 3F comprise log FITC fluorescence versus Transformed OLS, FIG. 3G comprise log FITC fluorescence versus OLS and FIG. 3H comprises log FITC fluorescence versus transformed OLS.
Figure 3B:
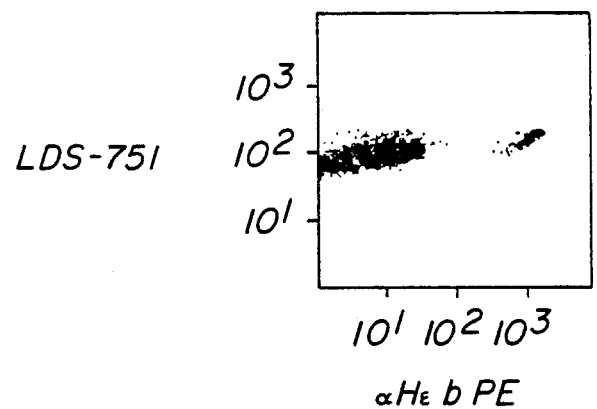
Figure 3C:
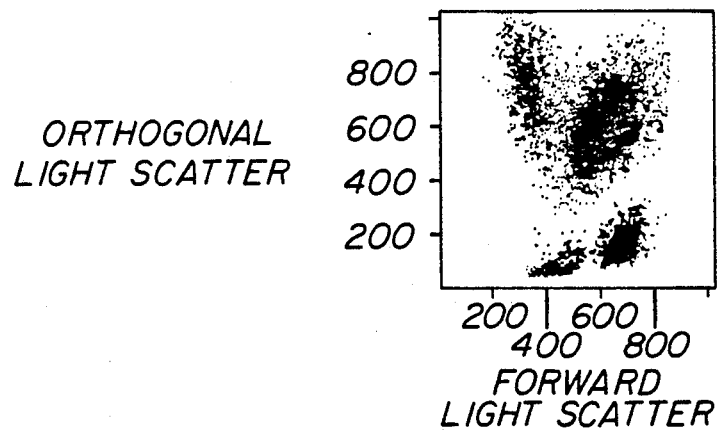
Figure 3D:
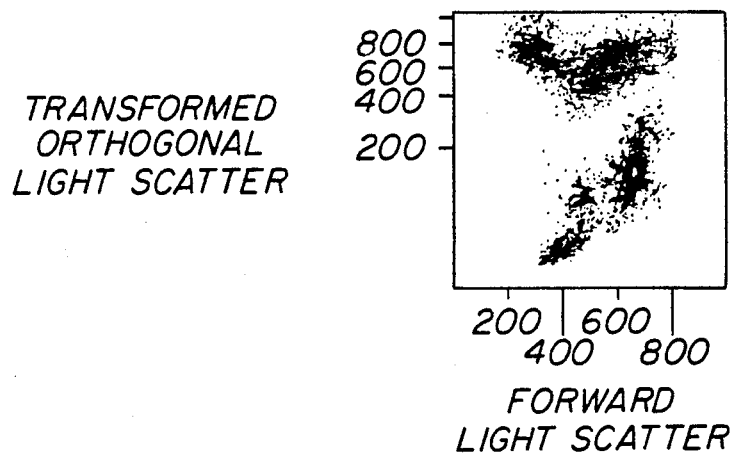
Figure 3E:
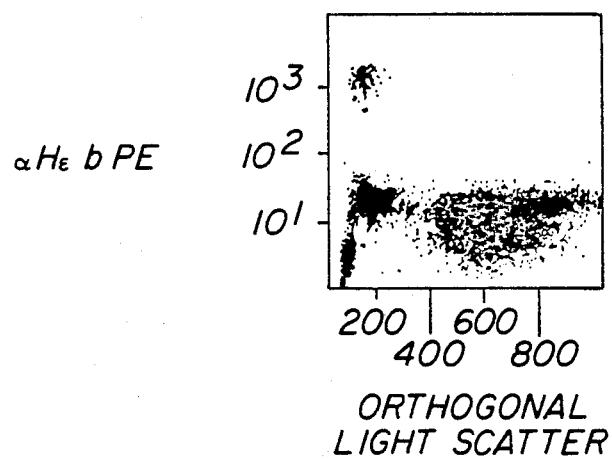
Figure 3F:
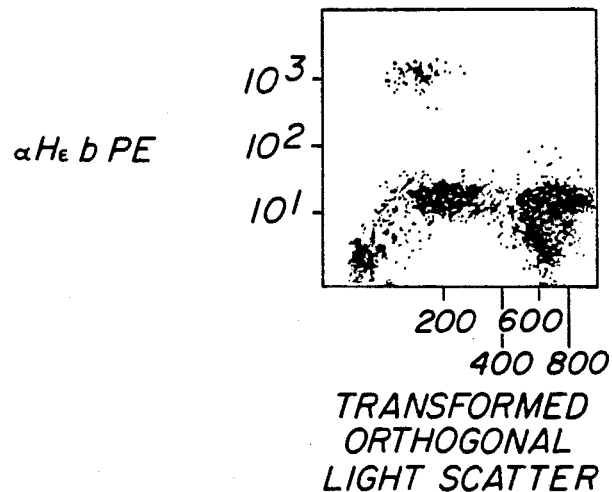
Figure 3G:
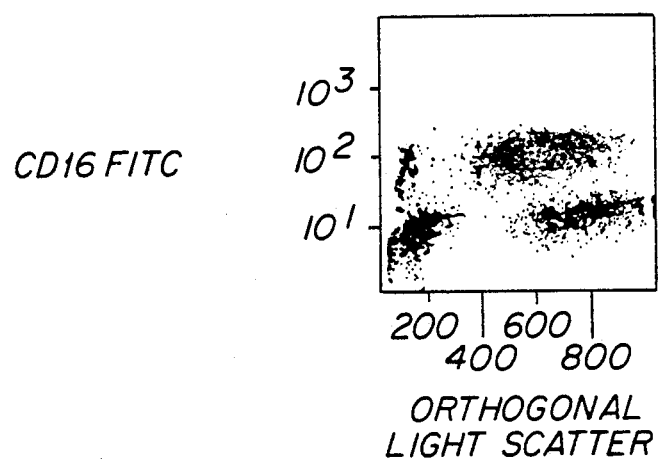
Figure 3H:
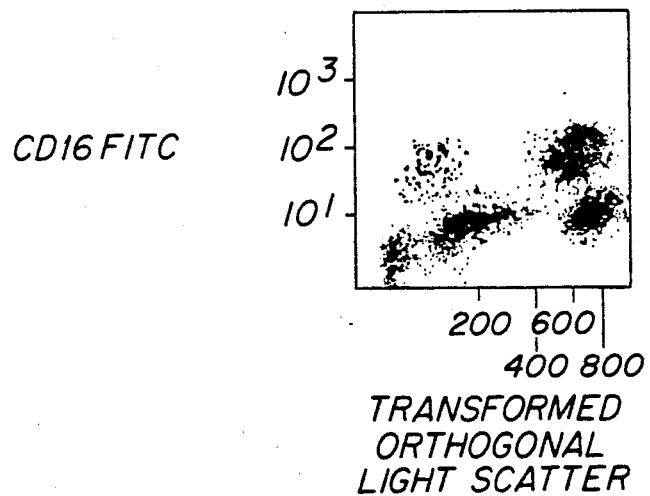

Turning to FIG. 3A, this method of transformation was applied to peripheral blood samples prepared as above but stained with anti-CD16 FITC (to identify NK cells and neutrophils) and anti human IgE biotin/PE (to identify basophils). LDS-751 was used as in FIG. 1 to gate on intact nucleated cells. See FIG. 3B. Using the Paint-A-Gate software, neutrophils were colored green, eosinophils were colored violet, basophils were colored light blue, monocytes were colored red, CD16+ NK cells were colored black and lymphocytes were colored yellow. In the traditional displays of OLS vs. FLS (FIG. 3C), anti human IgE biotin/PE vs. OLS (FIG. 3E) and CD16 FITC vs. OLS (FIG. 3G), the neutrophils and eosinophils dominate the display while the data for lymphocytes, basophils and monocytes are compacted. By applying the transformation method described above, the lymphocyte, basophil and monocyte regions are emphasized in the transformed OLS displays (FIG. 3D, F and H) resulting in a more even distribution of leukocyte populations across the display.

It should be noted that in the above examples OLS was used as the transformed parameter; however, this method is not limited to the transformation of OLS but may be used to transform FLS as well as any of the fluorescence parameters. In fact, it is possible to transform more than one parameter using the above method. In such a case, each parameter can be transformed separately, as above, but the results may be plotted on a transformed versus transformed basis.

Figure 4:
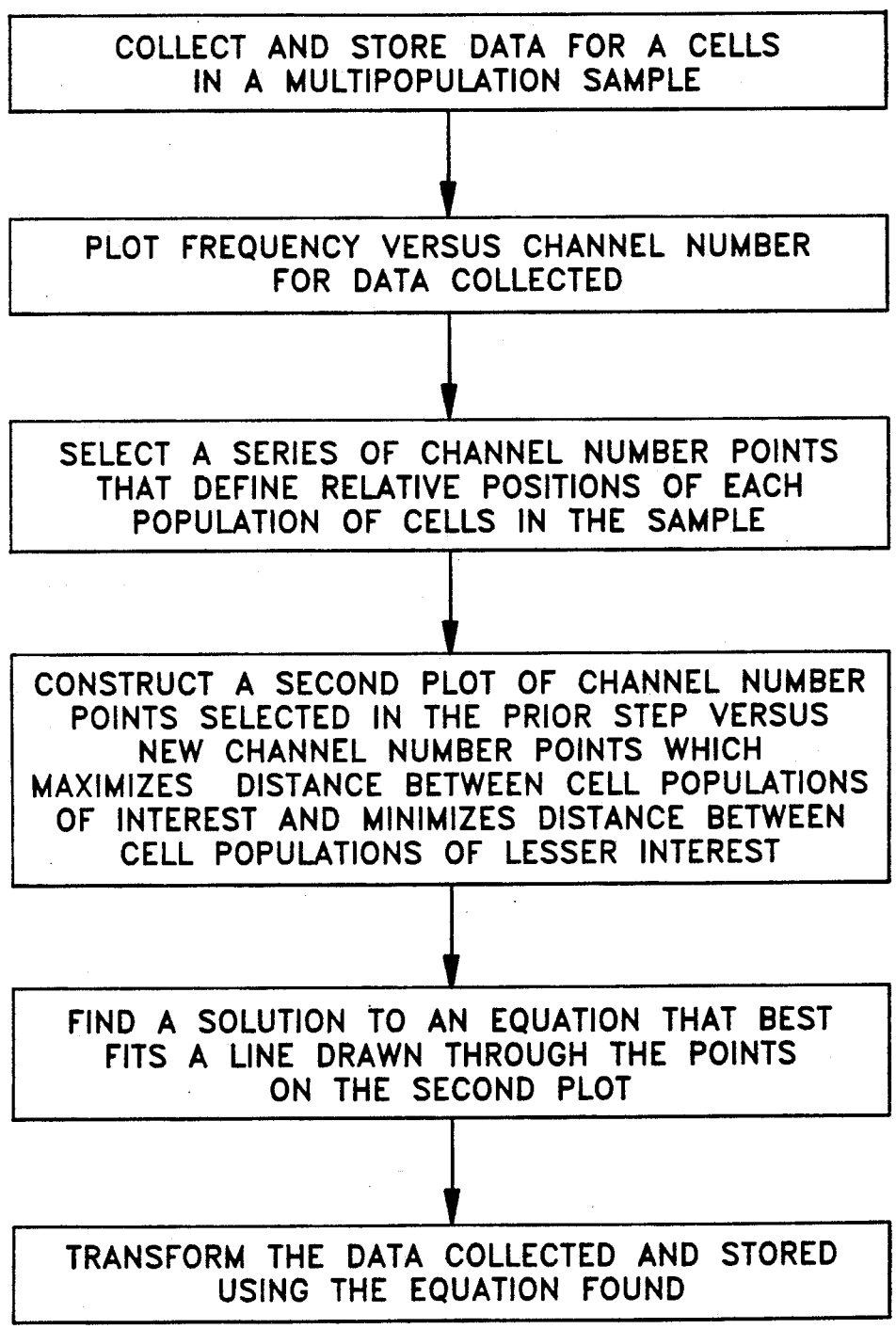
FIG. 4 is a flow chart of the steps comprising a method of data transformation in accordance with this invention.

It also should be appreciated that the plotting of the frequency of cells in the sample against channel number for any parameter need not be done manually, nor need the selection of the points be done manually. It will be recognized that certain populations will have certain mean channel values for different parameters. Accordingly, selecting of the points to define different populations can be done automatically by programming in those values. In fact, the entire process can be automated using the appropriate combination of hardware and software. FIG. 4 is a flow chart of the steps that comprise the method of this invention.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

We claim:

1. A method to transform one or more parameters of data on a non-linear or non-logarithmic basis gathered for a sample containing more than one population of cells comprising, for each parameter of data to be transformed, the steps of plotting frequency versus channel number, selecting a series of channel number points such that the points define the relative position of each population of cells in the sample, constructing a second plot of channel number for the points selected and plotting those points on a new arbitrary channel number axis such that the distance between populations of interest is maximized while the distance between populations of lesser interest is minimized, finding an equation that best fits a line drawn through the points on the second plot and transforming the data using the equation found.

2. The method of claim 1 wherein the data is gathered by means of flow cytometry.

3. The method of claim 1 wherein the sample is taken from blood.

4. The method of claim 1 wherein the sample is taken from bone marrow.

5. The method of claim 1 wherein the parameters are selected from the group consisting of light scatter and fluorescence.

6. The method of claim 5 wherein one of the parameters is immunofluorescence.

7. The method of claim 5 wherein the light scatter parameters include orthogonal and forward light scatter.

8. The method of claim 7 wherein one of the parameters is orthogonal light scatter.

9. A method to transform orthogonal light scatter data on a non-linear or non-logarithmic basis gathered from a sample containing more than one population of cells comprising the steps of plotting frequency versus channel number for orthogonal light scatter, selecting a series of channel number points for orthogonal light scatter such that the points define the relative position of each population of cells in the sample, constructing a second plot of channel number for the points selected and plotting those points on a new arbitrary channel number axis such that the distance between populations of interest is maximized while the distance between populations of lesser interest is minimized, finding an equation that best fits a line drawn through the points on the second plot and transforming the data using the equation found.

10. The method of claim 9 wherein the data is gathered by means of flow cytometry.

* * * * *